(12) United States Patent
Iverson et al.

(10) Patent No.: US 7,745,146 B2
(45) Date of Patent: Jun. 29, 2010

(54) COMPOSITIONS AND METHODS FOR DIAGNOSING PATIENTS WITH ACUTE ATHEROSCLEROTIC SYNDROME

(75) Inventors: G. Michael Iverson, Del Mar, CA (US); Walter L. Binder, San Diego, CA (US); Gary L. Norman, San Clemente, CA (US)

(73) Assignee: Inova Diagnostics, Inc., San Diego, CA (US)

( * ) Notice: Subject to any disclaimer, the term of this patent is extended or adjusted under 35 U.S.C. 154(b) by 2 days.

(21) Appl. No.: 11/881,426

(22) Filed: Jul. 26, 2007

(65) Prior Publication Data
US 2008/0153115 A1 Jun. 26, 2008

Related U.S. Application Data

(60) Provisional application No. 60/833,757, filed on Jul. 26, 2006, provisional application No. 60/918,225, filed on Mar. 14, 2007.

(51) Int. Cl.
*G01N 33/53* (2006.01)
*G01N 33/564* (2006.01)
*G01N 33/543* (2006.01)

(52) U.S. Cl. ................ 435/7.1; 435/7.92; 435/7.93; 435/7.95; 435/69.3; 436/506; 436/513; 436/518; 530/387.9

(58) Field of Classification Search ................ 435/7.1, 435/7.92, 7.93, 7.95, 69.3; 436/506, 518, 436/71, 513; 530/359, 387.9, 391.3
See application file for complete search history.

(56) References Cited

U.S. PATENT DOCUMENTS

| | | | |
|---|---|---|---|
| 4,981,785 A | 1/1991 | Nayak |
| 5,358,691 A | 10/1994 | Clark et al. |
| 5,885,530 A | 3/1999 | Babson et al. |
| 6,159,750 A | 12/2000 | Edmonds |
| 6,585,210 B1 | 7/2003 | Lee |

OTHER PUBLICATIONS

Veres et al., 2004. Antiphospholipid antibodies in acute coronary syndrome. Lupus 13: 423-427.*
Lopez et al., 2004. Anti-beta2-glycoprotein I and antiphosphatidylserine antibodies are predictors of arterial thrombosis in patients with antiphospholipid syndrome. American Journal Clinical Pathology 121: 142-149.*
Blank M, et al., Prevention of experimental antiphospholipid syndrome and endothelial cell activation by synthetic peptides, 1999, *PNAS* 96:5164-8.
Hunt J., et al., Identification of a region of beta 2-glycoprotein I critical for lipid binding and anti-cardiolipin antibody cofactor activity, 1993, *PNAS* 90:2141-5.
Igarashi M., et al, Human beta2-glycoprotein I as an anticardiolipin cofactor determined using mutants expressed by a baculovirus system, 1996, *Blood*, 87 (8): 3262-70.
Iverson GM, et al., Anti-B2 glycoprotein I (B2GPI) autoantibodies recognize an epitope on the first domain of B2GPI, 1998, *PNAS* 95:15542-15546.
Iverson GM, et al., The orientation of beta2GPI on the plate is important for the binding of anti-beta2GPI autoantibodies by ELISA, 2002, *J. of Autoimmunity*, 18: 289-297.
Iverson GM, et al., Use of single point mutations in domain I of beta 2-glycoprotein I to determine fine antigenic specificity of antiphospholipid, J. Immunol. 169: 7097-7103, 2002.
Iverson GM et al, Patients with atherosclerotic syndrome, negative in anti-cardiolipin assays, make IgA autoantibodies that preferentially target domain 4 or, J. Autoimmunity 27: 266-271, 2006.
George J, et al, Target recognition of beta2-glycoprotein I (beta2GPI)-dependent anticardiolipin antibodies: evidence for involvement of the fourth domain of beta2GPI in antibody binding, 1998, *J Immunol.* 160(8):3917-3923.
Greco TP, et al., Testing for the antiphospholipid syndrome: importance of IgA anti-beta 2-glycoprotein I, 2000, *Lupus*, 9:33-41.
Kahles T, et al., Phosphatidylserine IgG and beta-2-glycoprotein I IgA antibodies may be a risk factor for ischaemic stroke, 2005, *Rheumatology* 44(9):1161-5.
Kasahara H, et al., Antigenic structures recognized by anti-beta2-glycoprotein I auto-antibodies, 2005, Int. Immuno.I 17:1533-42.
Koike T, et al., Beta 2-glycoprotein I-anti-beta 2-glycoprotein I interaction, 2000, J. Autoimmun 15: 97-100.
Lozier J. et al., Complete amino acid sequence of human plasma beta 2-glycoprotein I, 1984, PNAS 81:3640-4.
McNeeley PA, et al., Beta2-glycoprotein I-dependent anticardiolipin antibodies preferentially bind the amino terminal domain of beta2-glycoprotein I, 2001, Thromb Haemost 86:590-5.
Ranzolin A, et al., Anti-beta2-glycoprotein I antibodies as risk factors for acute myocardial infarction, 2004 Arg Bras Cardiol. 83(2):141-4; 137-40.
Staub HL, et al., Antibodies to the atherosclerotic plaque components beta2-glycoprotein I and heat-shock proteins as risk factors for acute cerebral ischemia, 2003, Arq. Neuropsiquiat 61(3B):757-63.
Yang CD, et al., The fifth domain of B2-glycoprotein I contains antigenic epitopes recognized by anticardiolipin antibodies derived from patients with the antiphospholipid syndrome, 1997, APLAR J Rheumatol 1:96-100.
Takatsu et al., "Acute myocardial infarction associated with systemic lupus erythematosus documented by coronary arteriograms." Chest, 1985:88:147-149.
Takeuchi et al., "Primary antiphospholipid syndrome with acute myocardial infarction recanalised by PTCA." Heart, 1998:79:96-98.

\* cited by examiner

*Primary Examiner*—Shafiqul Haq
*Assistant Examiner*—James L Grun
(74) *Attorney, Agent, or Firm*—The Nath Law Group; Laurie A. Axford

(57) ABSTRACT

The present invention is in the field of autoimmunity. More specifically, the present invention relates to the detection of autoantibodies to domain 4 of beta 2-glycoprotein I ($\beta_2$-GPI) as an indicator for atherosclerosis.

1 Claim, 3 Drawing Sheets

SEQUENCE LISTING

<160> NUMBER OF SEQ ID NOS: 6

<210> SEQ ID NO 1
<211> LENGTH: 326
<212> TYPE: PRT
<213> ORGANISM: Homo sapiens

<400> SEQUENCE: 1

Gly Arg Thr Cys Pro Lys Pro Asp Asp Leu Pro Phe Ser Thr Val Val
1               5                   10                  15

```
Pro Leu Lys Thr Phe Tyr Glu Pro Gly Glu Glu Ile Thr Tyr Ser Cys
            20                  25                  30

Lys Pro Gly Tyr Val Ser Arg Gly Gly Met Arg Lys Phe Ile Cys Pro
        35                  40                  45

Leu Thr Gly Leu Trp Pro Ile Asn Thr Leu Lys Cys Thr Pro Arg Val
    50                  55                  60

Cys Pro Phe Ala Gly Ile Leu Glu Asn Gly Ala Val Arg Tyr Thr Thr
65                  70                  75                  80

Phe Glu Tyr Pro Asn Thr Ile Ser Phe Ser Cys Asn Thr Gly Phe Tyr
                85                  90                  95

Leu Asn Gly Ala Asp Ser Ala Lys Cys Thr Glu Gly Lys Trp Ser
            100                 105                 110

Pro Glu Leu Pro Val Cys Ala Pro Ile Ile Cys Pro Pro Ser Ile
            115                 120                 125

Pro Thr Phe Ala Thr Leu Arg Val Tyr Lys Pro Ser Ala Gly Asn Asn
    130                 135                 140

Ser Leu Tyr Arg Asp Thr Ala Val Phe Glu Cys Leu Pro Gln His Ala
145                 150                 155                 160

Met Phe Gly Asn Asp Thr Ile Thr Cys Thr Thr His Gly Asn Trp Thr
                165                 170                 175

Lys Leu Pro Glu Cys Arg Glu Val Lys Cys Pro Phe Pro Ser Arg Pro
            180                 185                 190

Asp Asn Gly Phe Val Asn Tyr Pro Ala Lys Pro Thr Leu Tyr Tyr Lys
            195                 200                 205

Asp Lys Ala Thr Phe Gly Cys His Asp Gly Tyr Ser Leu Asp Gly Pro
    210                 215                 220

Glu Glu Ile Glu Cys Thr Lys Leu Gly Asn Trp Ser Ala Met Pro Ser
225                 230                 235                 240

Cys Lys Ala Ser Cys Lys Val Pro Val Lys Lys Ala Thr Val Val Tyr
                245                 250                 255

Gln Gly Glu Arg Val Lys Ile Gln Glu Lys Phe Lys Asn Gly Met Leu
            260                 265                 270

His Gly Asp Lys Val Ser Phe Phe Cys Lys Asn Lys Glu Lys Lys Cys
        275                 280                 285

Ser Tyr Thr Glu Asp Ala Gln Cys Ile Asp Gly Thr Ile Glu Val Pro
    290                 295                 300

Lys Cys Phe Lys Glu His Ser Ser Leu Ala Phe Trp Lys Thr Asp Ala
305                 310                 315                 320

Ser Asp Val Lys Pro Cys
                325

<210> SEQ ID NO 2
<211> LENGTH: 64
<212> TYPE: PRT
<213> ORGANISM: Homo sapiens

<400> SEQUENCE: 2

Gly Arg Thr Cys Pro Lys Pro Asp Asp Leu Pro Phe Ser Thr Val Val
1               5                   10                  15

Pro Leu Lys Thr Phe Tyr Glu Pro Gly Glu Glu Ile Thr Tyr Ser Cys
            20                  25                  30

Lys Pro Gly Tyr Val Ser Arg Gly Gly Met Arg Lys Phe Ile Cys Pro
        35                  40                  45

Leu Thr Gly Leu Trp Pro Ile Asn Thr Leu Lys Cys Thr Pro Arg Val
```

```
              50                  55                  60

<210> SEQ ID NO 3
<211> LENGTH: 62
<212> TYPE: PRT
<213> ORGANISM: Homo sapiens

<400> SEQUENCE: 3

Thr Pro Arg Val Cys Pro Phe Ala Gly Ile Leu Glu Asn Gly Ala Val
1               5                   10                  15

Arg Tyr Thr Thr Phe Glu Tyr Pro Asn Thr Ile Ser Phe Ser Cys Asn
            20                  25                  30

Thr Gly Phe Tyr Leu Asn Gly Ala Asp Ser Ala Lys Cys Thr Glu Glu
        35                  40                  45

Gly Lys Trp Ser Pro Glu Leu Pro Val Cys Ala Pro Ile Ile
    50                  55                  60

<210> SEQ ID NO 4
<211> LENGTH: 67
<212> TYPE: PRT
<213> ORGANISM: Homo sapiens

<400> SEQUENCE: 4

Ala Pro Ile Ile Cys Pro Pro Ser Ile Pro Thr Phe Ala Thr Leu
1               5                   10                  15

Arg Val Tyr Lys Pro Ser Ala Gly Asn Asn Ser Leu Tyr Arg Asp Thr
            20                  25                  30

Ala Val Phe Glu Cys Leu Pro Gln His Ala Met Phe Gly Asn Asp Thr
        35                  40                  45

Ile Thr Cys Thr Thr His Gly Asn Trp Thr Lys Leu Pro Glu Cys Arg
    50                  55                  60

Glu Val Lys
65

<210> SEQ ID NO 5
<211> LENGTH: 63
<212> TYPE: PRT
<213> ORGANISM: Homo sapiens

<400> SEQUENCE: 5

Arg Glu Val Lys Cys Pro Phe Pro Ser Arg Pro Asp Asn Gly Phe Val
1               5                   10                  15

Asn Tyr Pro Ala Lys Pro Thr Leu Tyr Tyr Lys Asp Lys Ala Thr Phe
            20                  25                  30

Gly Cys His Asp Gly Tyr Ser Leu Asp Gly Pro Glu Glu Ile Glu Cys
        35                  40                  45

Thr Lys Leu Gly Asn Trp Ser Ala Met Pro Ser Cys Lys Ala Ser
    50                  55                  60

<210> SEQ ID NO 6
<211> LENGTH: 85
<212> TYPE: PRT
<213> ORGANISM: Homo sapiens

<400> SEQUENCE: 6

Lys Ala Ser Cys Lys Val Pro Val Lys Lys Ala Thr Val Val Tyr Gln
1               5                   10                  15

Gly Glu Arg Val Lys Ile Gln Glu Lys Phe Lys Asn Gly Met Leu His
            20                  25                  30
```

```
Gly Asp Lys Val Ser Phe Phe Cys Lys Asn Lys Glu Lys Lys Cys Ser
        35                  40              45

Tyr Thr Glu Asp Ala Gln Cys Ile Asp Gly Thr Ile Glu Val Pro Lys
    50                  55              60

Cys Phe Lys Glu His Ser Ser Leu Ala Phe Trp Lys Thr Asp Ala Ser
65              70                  75              80

Asp Val Lys Pro Cys
                85
```

COMPOSITIONS AND METHODS FOR DIAGNOSING PATIENTS WITH ACUTE ATHEROSCLEROTIC SYNDROME

CROSS-REFERENCE TO RELATED APPLICATIONS

This application claims the priority benefit of U.S. provisional patent application Ser. No. 60/833,757 filed Jul. 26, 2006 and U.S. provisional patent application Ser. No. 60/918,225 filed Mar. 14, 2007, each of which is hereby incorporated by reference in its entirety.

TECHNICAL FIELD

The present invention is in the field of autoimmunity. More specifically, the present invention relates to the detection of autoantibodies to domain 4 of beta 2-glycoprotein I ($\beta_2$-GPI) as an indicator for atherosclerosis.

BACKGROUND OF THE INVENTION

IgA class autoantibodies to beta 2-glycoprotein I ($\beta_2$-GPI) have recently been reported in patients with acute myocardial infarction and also in patients with ischemic stroke (Ranzolin A, et al., *Arg Bras Cardiol.* 83(2):141-4; 137-40 (2004); Kahles T, et al., *Rheumatology* 44(9):1161-5 (2005); Staub H L, et al., *Arg Neuropsiquiat* 61(3B):757-63 (2003)). A striking observation from two of these studies was that the IgA $\beta_2$-GPI autoantibodies were usually detected in patients that were negative for IgA anti-cardiolipin antibodies (ACA) (Ranzolin A, et al., *Arg Bras Cardiol.* 83(2):141-4; 137-40 (2004); Staub H L, *Arg Neuropsiquiat* 61(3B):757-63 (2003)). This finding is in sharp contrast to that observed in patients with anti-phospholipid syndrome (APS), where both anti-$\beta_2$-GPI and anti-cardiolipin antibodies are usually positive.

$\beta_2$-GPI is a serum protein composed of five homologous domains numbered 1-5 from the N terminus. Domains 1-4 are composed of ~60 amino acids that contain a motif characterized by a framework of four conserved cysteine residues, which form two internal disulfide bridges (Lozier, J. et al., *PNAS* 81:3640-3644 (1984)). The fifth domain differs from domains 1-4 in that it contains 82 amino acid residues with six cysteines. The fifth domain contains the phospholipid binding site (Hunt, J., et al., *PNAS* 90:2141-2145 (1993)).

Conflicting findings have been published concerning the domain specificity of anti-$\beta_2$-GPI autoantibodies. For example, in one study, it was shown that using recombinant-$\beta_2$-GPI and $\beta_2$-GPI domain-deleted mutants (Dms) expressed in insect cells, that anti-$\beta_2$-GPI autoantibodies found in serum samples from patients with APS recognize domain 1 of $\beta_2$-GPI (Iverson, G M, et al., *PNAS* 95:15542-15546 (1998).

There are also reports that IgG anti-$\beta_2$-GPI autoantibodies in patients with APS recognize epitopes on domains 3, 4 and 5 of $\beta_2$-GPI (Blank, M, et al., *PNAS* 96:5164-8 (1999); Blank, M, et al., *PNAS* 96:5164-8 (1999); Koike T, et al., *J. Autoimmun* 15: 97-100 (2000); Yang C D, et al., *APLAR J Rheumatol* 1:96-100 (1997); Iverson, G M, et al., *J. of Autoimmunity* 18:289-297 (2002); and McNeeley P A, et al., *Thromb Haemost* 86:590-5 (2001)).

Accordingly, there is a need for an enhanced understanding of the antibody profiles exhibited by APS patients (cardiolipin IgG positive/$\beta_2$-GPI IgG/IgA positive), and the differences between these profiles and the profiles exhibited by cardiovascular patients with acute ischemic disease (cardiolipin IgG/IgA negative/$\beta_2$-GPI IgA positive), which is based on differing domain-specificity of the APS and cardiovascular patient's antibodies. The present invention provides such an enhanced understanding, and relates to the finding that IgA anti-$\beta_2$-GPI autoantibodies that bind to domain 4 are found in a high percentage of patients with acute atherosclerotic syndrome (ASS).

SUMMARY OF THE INVENTION

The present invention relates, in part, to a method for diagnosing a subject suspected of having acute atherosclerotic syndrome (AAS) comprising the steps of: preparing an antigen comprising a polypeptide having an epitope from domain 4 of $\beta_2$-GPI; reacting the antigen with a biological sample from the subject; and detecting IgA antibodies in the sample that bind to the antigen.

The antigen according to the present invention may consist of domain 4 in its entirety, or an antigenic fragment of domain 4, and/or it may include all or a portion of the sequences of domains 2, 3 and 5. Accordingly, the phrase "an epitope from domain 4" intends that the epitope is recognized by an antibody that is selective for domain 4, in that it binds preferentially to domain 4 when compared to the other 4 domains. Thus, the epitope may be a polypeptide consisting of domain 4 (or a fragment thereof) alone, or a combination of domains 2, 3 and 4; 2, 3, 4 and 5; 3 and 4; 4 and 5; 3, 4 and 5; and/or fragments thereof.

As shown below, the domain 4 sequence consists of 56 amino acids. Given that the minimum number of contiguous amino acids from domain 4 is in the neighborhood of 6 it is also possible to construct an antigen that is a multimer (such as a dimer, trimer, etc.) of the domain 4 epitope, with the repeating units separated by non-interfering linking regions such as polyglycine and other small nonpolar amino acids. Such linking regions may or may not include the naturally existing flanking sequences of the epitope.

According to one embodiment, the invention is a method of diagnosing an acute atherosclerotic syndrome in a subject, comprising determining the presence or absence of IgA domain 4-specific anti-beta 2-glycoprotein I ($\beta_2$-GPI) antibodies in said subject, wherein the presence of said IgA anti-$\beta_2$-GPI antibodies indicates that said subject has an acute atherosclerotic syndrome.

In an alternative embodiment, the invention is a method of diagnosing an acute atherosclerotic syndrome in a subject, comprising the steps of: a. obtaining a sample from a subject suspected of having an acute atherosclerotic syndrome; b. contacting the sample with a $\beta_2$-GPI antigen comprising a domain 4 epitope; and c. detecting the presence or absence of IgA domain 4-specific anti-$\beta_2$-GPI antibodies that bind to the domain 4 epitope; wherein the presence of said IgA domain 4-specific anti-$\beta_2$-GPI antibodies in said sample indicates that said subject has an acute atherosclerotic syndrome.

In yet another embodiment, the invention is a method of diagnosing an acute atherosclerotic syndrome in a subject, comprising the steps of: a. contacting a sample from a subject suspected of having an acute atherosclerotic syndrome with an epitope derived from domain 4 of a $\beta_2$-GPI antigen comprising the amino acid sequence of SEQ ID NO:5 without linker sequences under conditions suitable to form a complex of the epitope and IgA domain 4-specific anti-$\beta_2$-GPI antibody; and b. detecting the presence or absence of the IgA domain 4-specific anti-$\beta_2$-GPI antibody in the complex, wherein the presence of said domain 4-specific IgA anti-$\beta_2$-GPI antibodies in said subject indicates that said subject has an acute atherosclerotic syndrome.

The method for detecting the IgA anti-$\beta_2$-GPI antibodies can be by any known method, such as with a labeled anti-IgA antibody in a variety of well known assay formats such as an enzyme-linked immunosorbent assay.

In one embodiment, the method further includes determining the presence or absence of anticardiolipin (aCL) antibodies in said subject, wherein the presence of said domain 4-specific IgA anti-$\beta_2$-GPI antibodies in said subject and the absence of anticardiolipin (aCL) antibodies indicates that said subject has an acute atherosclerotic syndrome.

The domain 4 epitope may exist in the form of a variety of different combinations of domains and fragments thereof. For example, the domain 4 epitope may consist of the known domain 4 fragment antigenic sequence that is adjacent to domain 5 (Kasahara, et al.). It may also be in the form of the full domain 4 plus 5 sequences with all or portion of domain 3, or it may be in the form of the full domain 3, 4 and 5 sequences with all or a portion of domain 2, or it may be in the form of adjacent fragments of domain 4 and 5, and so on. However, in a preferred embodiment, domain 1 is completely absent.

Other aspects of the invention are described throughout the specification.

DETAILED DESCRIPTION

Figure 1:
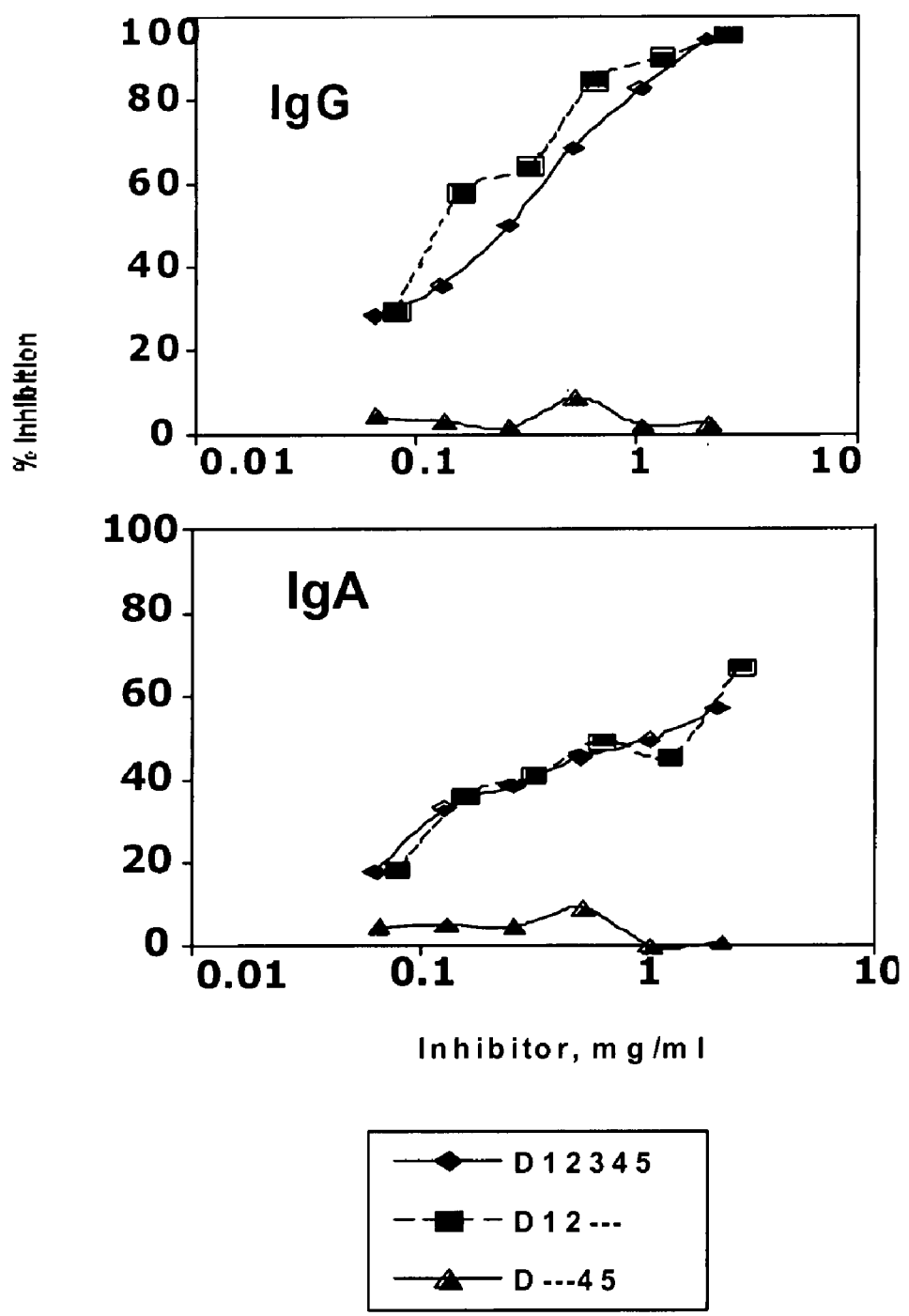
FIG. 1 depicts: Competitive inhibition of APS sample 6635 binding to $\beta_2$-GPI by Recombinant $\beta_2$-GPI and Dms. A constant amount of antibody was mixed with varying concentrations of inhibitor in wells coated with $\beta_2$-GPI. Recombinant $\beta_2$-GPI and DMs were used as inhibitors. Upper panel measures inhibition of IgG antibodies. Lower panel measures inhibition of IgA antibodies.

In the description that follows, a number of terms used in the field of molecular biology, immunology and medicine are extensively utilized. In order to provide a clearer and consistent understanding of the specification and claims, including the scope to be given such terms, the following non-limiting definitions are provided.

When the terms "one," "a," or "an" are used in this disclosure, they mean "at least one" or "one or more," unless otherwise indicated.

The term "antibody" refers to a molecule which is capable of binding an epitope or antigenic determinant. The term "antibody" includes whole antibodies and antigen-binding fragments thereof, including single-chain antibodies. Such antibodies include human antigen binding antibody and antibody fragments, including, but not limited to, Fab, Fab' and F(ab')$_2$, Fd, single-chain Fvs (scFv), single-chain antibodies, disulfide-linked Fvs (sdFv) and fragments comprising either a $V_L$ or $V_H$ domain. The antibodies may be from any animal origin including birds and mammals, e.g., human, murine, rabbit, goat, guinea pig, camel, horse and the like.

The term "antigen" refers to a molecule capable of being bound by an antibody or a T cell receptor (TCR) if presented by MHC molecules. An antigen may be additionally capable of being recognized by the immune system and/or being capable of inducing a humoral immune response and/or cellular immune response leading to the activation of B- and/or T-lymphocytes. An antigen may have one or more epitopes (B- and T-epitopes). Antigens as used herein may also be mixtures of several individual antigens.

The term "antigenic determinant" refers to a portion of an antigen that is specifically recognized by either B- or T-lymphocytes. Antigenic determinants or epitopes are those parts of an antigen that are recognized by antibodies, or in the context of an MHC, by T-cell receptors. An antigenic determinant contains one or more epitopes.

The term "autoantigen" refers to a constituent of self that binds an autoantibody or that induces a cellular response.

The term "autoantibody" refers to an immunoglobulin, antigen specific B cell surface receptor (surface immunoglobulin), or antigen specific T cell receptor directed against self-protein, carbohydrate or nucleic acid.

The term "epitope" refers to a portion of an antigen that is recognized by the immune system, specifically by an antibody (e.g., an autoantibody), B-cell, or T cell, and thus the particular domain, region or molecular structure to which the antibody, B-cell or T-cell binds. An antigen may consist of numerous epitopes while a hapten, typically, may possess few epitopes.

The term "wild-type" refers to a gene or gene product isolated from a naturally occurring source. A wild-type gene is that which is most frequently observed in a population and is thus arbitrarily designed the "normal" or "wild-type" form of the gene or gene product. In contrast, the term "modified" or "mutant" refers to a gene or gene product that displays modifications in sequence and or functional properties (i.e., altered characteristics, e.g., hypomethylation) when compared to the wild-type gene or gene product. It is noted that naturally occurring mutants can be isolated; these are identified by the fact that they have altered characteristics, such as physical and biological properties, when compared to the wild-type gene or gene product.

The term "native protein" refers to a protein that contains only those amino acids found in the protein as it occurs in nature. A native protein may be produced by recombinant means or may be isolated from a naturally occurring source.

The term "fragment" means a peptide, polypeptide, or compound containing naturally occurring amino acids, non-naturally occurring amino acids or chemically modified amino acids. The fragments may range in size from two amino acid residues to the entire amino acid sequence minus one amino acid.

The term "subject" refers to an animal, including, but limited to, an ave, ovine, bovine, ruminant, lagomorph, porcine, equine, canine, feline, rodent or primate, for example a human. Typically, the terms "subject" and "patient" are used interchangeably herein in reference to a mammalian subject, particularly a human subject.

The term "sample" is used in its broadest sense. In one sense, it is meant to include a specimen or culture obtained from any source, as well as biological and environmental samples. Biological samples may be obtained from animals (including humans) and refers to a biological material or compositions found therein, including, but not limited to, bone marrow, blood, serum, platelet, plasma, interstitial fluid, urine, cerebrospinal fluid, nucleic acid, DNA, tissue, and purified or filtered forms thereof.

The term "serum sample" refers to a biological sample comprising serum. It is understood that a serum sample for use in the present methods may contain other components, in particular blood components. Thus, whole blood samples, or blood samples which have been only partially fractionated or separated but which still contain serum, are considered "serum samples" for purposes of the present invention. One skilled in the art can readily obtain serum samples, for example by using conventional blood drawing techniques. Furthermore, the presence of preservative, anticoagulants or other chemicals in the serum sample should not interfere the detection of IgA $\beta_2$-GPI antibodies.

The term "control" or "control sample" refers to one or more sample, such as a serum sample, taken from at least one healthy blood donor. It is understood that when the control comprises multiple samples, the IgA $\beta_2$-GPI-specific antibody level can be expressed as the arithmetic mean, median, mode or other suitable statistical measure of the IgA $\beta_2$-GPI-specific antibody level measured in each sample. Multiple control samples can also be pooled, and IgA $\beta_2$-GPI-specific antibody level of the pooled samples can be determined and compared to the subject's sample.

Atherosclerosis (also referred to as arteriosclerosis, atheromatous vascular disease, arterial occlusive disease) as used herein, refers to a cardiovascular disease characterized by plaque accumulation on vessel walls and vascular inflammation. The plaque consists of accumulated intracellular and extracellular lipids, smooth muscle cells, connective tissue, inflammatory cells, and glycosaminoglycans. Inflammation occurs in combination with lipid accumulation in the vessel wall, and vascular inflammation is with the hallmark of atherosclerosis disease process.

The term "acute atherosclerotic syndrome" or "AAS" refers to several types of cardiovascular problems including, but not limited to, acute myocardial infarction, acute coronary syndrome, "carotid artery study," and peripheral artery disease.

Figure 3:
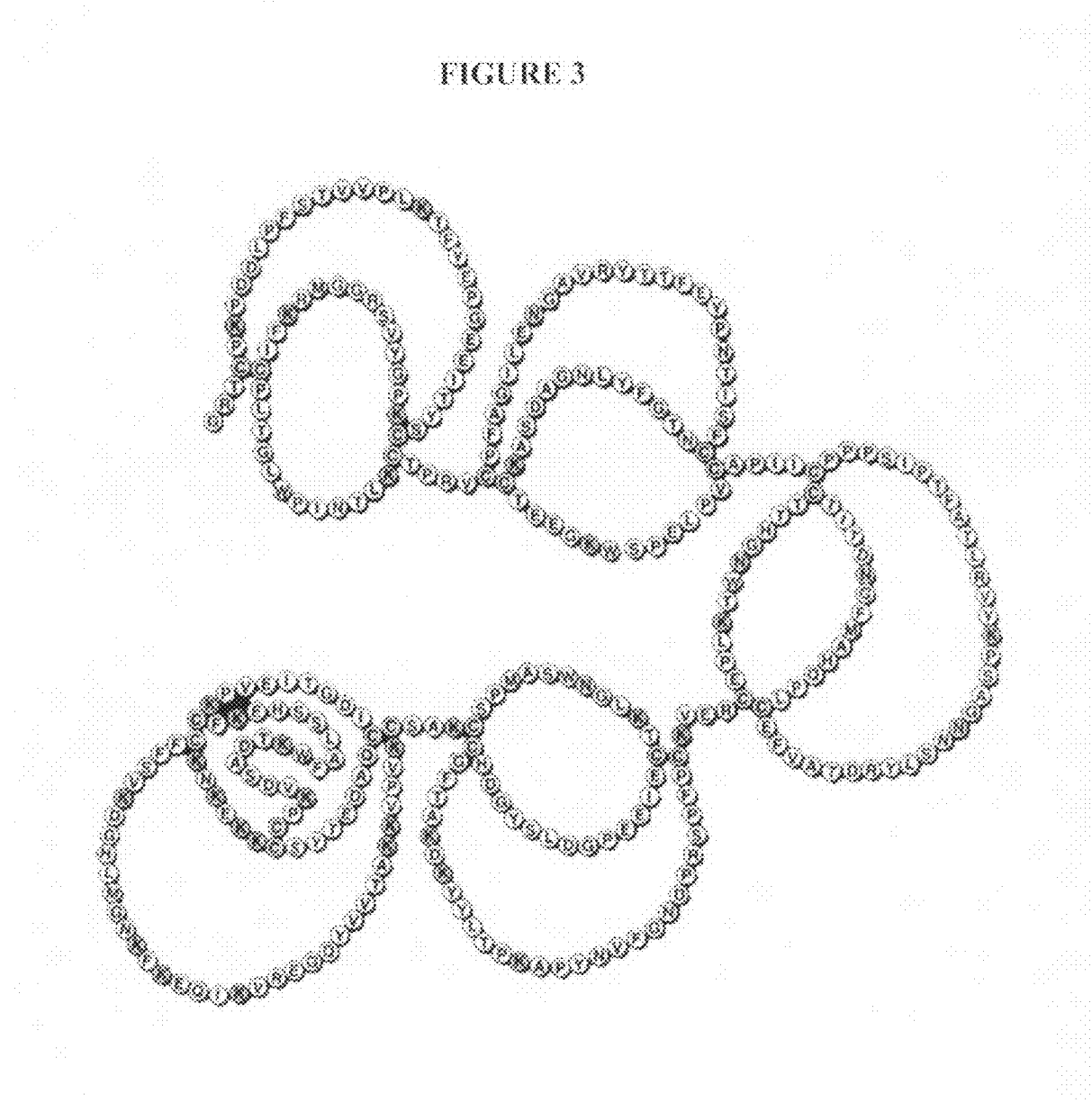
FIG. 3 depicts: The entire sequence and tertiary structure of $\beta_2$-GPI.

$\beta_2$-GPI is a serum protein composed of five homologous domains numbered 1-5 from the N terminus. The primary and predicted tertiary sequence is shown in FIG. 3. Domains 1-4 are composed of ~60 amino acids that contain a motif characterized by a framework of four conserved cysteine residues, which form two internal disulfide bridges. The fifth domain differs from domains 1-4 in that it contains 82 amino acid residues with six cysteines. The fifth domain contains the phospholipid binding site.

The amino acid sequence of domain 1 (SEQ ID NO.:2) as shown in FIG. 3, starting with the N-terminal end and ending with the small sequence that links domain 1 to domain 2 (underlined) is as follows:

GRTCPKPDDLPFSTVVPLKTFYEPGEEITYSCKPGYVSRGGMRKFICPLT
GLWPINTLKC<u>TPRV</u>

The amino acid sequence of domain 2 (SEQ ID NO.:3) as shown in FIG. 3, starting with the N-terminal end of the small sequence that links domain 1 to domain 2 (underlined) and ending with the small sequence that links domain 2 to domain 3 (underlined) is as follows:

<u>TPRV</u>CPFAGILENGAVRYTTFEYPNTISFSCNTGFYLNGADSAKCTEEGK
WSPELPVC<u>APII</u>

The amino acid sequence of domain 3 (SEQ ID NO.:4) as shown in FIG. 3, starting with the N-terminal end of the small sequence that links domain 2 to domain 3 (underlined) and ending with the small sequence that links domain 3 to domain 4 (underlined) is as follows:

<u>APII</u>CPPPSIPTFATLRVYKPSAGNNSLYRDTAVFECLPQHAMFGNDTIT
CTTHGNWTKLPEC<u>REVK</u>

The amino acid sequence of domain 4 (SEQ ID NO.:5) as shown in FIG. 3, starting with the N-terminal end of the small sequence that links domain 4 to domain 3 (underlined) and ending with the small sequence that links domain 4 to domain 5 (underlined) is as follows:

<u>REVK</u>CPFPSRPDNGFVNYPAKPTLYYKDKATFGCHDGYSLDGPEEIECTK
LGNWSAMPSC<u>KAS</u>

The amino acid sequence of domain 5 (SEQ ID NO.:6) as shown in FIG. 3, starting with the N-terminal end of the small sequence that links domain 4 to domain 5 (underlined) and ending with the C-terminal end is as follows:

<u>KAS</u>CKVPVKKATVVYQGERVKIQEKFKNGMLHGDKVSFFCKNKEKKCSYT
EDAQCIDGTIEVPKCFKEHSSLAFWKTDASDVKPC

As used herein, it shall be understood that the term "domain X" alone refers to a polypeptide with the amino acid sequence without the underlined linker sequences identified above, but when terms such as "domain X/Y" or "domain X+Y" are used, it refers to a polypeptide with the amino acid sequence of the two domains linked by the appropriate underlined linker sequence identified above. Likewise, referring to the "domain X amino acid sequence of SEQ. ID NO. A without linker sequences" means the same as saying the polypeptide that includes all of the SEQ. ID NO. A amino acids, without the underlined linker sequences identified above.

"Dms" or "domain-deleted mutants" nomenclature for domain deletion mutants uses numbers to indicate the presence of $\beta_2$-GPI domains, while a dash symbolizes the domain is missing. Thus D--345 is the name given to the recombinant protein that contains domains 3, 4 and 5 while lacking domains 1 and 2.

The $\beta_2$-GPI proteins of the present invention may also be its variants. Unless otherwise indicated, the term "$\beta_2$-GPI" refers both to native $\beta_2$-GPI proteins, as well as variants thereof. As used herein, $\beta_2$-GPI variants are $\beta_2$-GPI proteins which comprises an amino acid sequence having one or more amino acid substitutions, deletions, and/or additions (such as internal additions and/or $\beta_2$-GPI fusion proteins) as compared to the amino acid sequence of a native $\beta_2$-GPI proteins, but which nonetheless retain $\beta_2$-GPI immunologically activity. Such functionally or immunologically equivalent variants may occur as natural biological variations (e.g., polypeptide allelic variants, polypeptide orthologs, and polypeptide splice variants), or they may be prepared using known and standard techniques for example by chemical synthesis or modification, mutagenesis, e.g., site-directed or random mutagenesis, etc. Thus, for example, an amino acid may be replaced by another which preserves the physicochemical character of the $\beta_2$-GPI proteins or its epitope(s), e.g. in terms of charge density, hydrophilicity/hydrophobicity, size and configuration and hence preserve the immunological structure. "Addition" variants may include N- or C-terminal fusions as well as intrasequence insertion of single or multiple amino acids. Deletions may be intrasequence or may be truncations from the N- or C-termini.

The variants may have from 1 to 3, to 5, to 10, to 15, to 20, to 25, to 50, to 75, or to 100, or more than 100 amino acid substitutions, insertions, additions and/or deletions, wherein the substitutions may be conservative, or non-conservative, or a combination thereof. Additionally, the $\beta_2$-GPI proteins of the present invention may comprise at least 10, at least 12, at least 15, at least 20, at least 25, at least 30, at least 35, at least 40, or at least 50 consecutive amino acid residues of a native $\beta_2$-GPI protein. Such a variant is preferably at least about 50%, at least about 60%, at least about 70%, at least about 80%, as lest about 90%, or at least about 95% identical to a native $\beta_2$-GPI proteins. Furthermore, the $\beta_2$-GPI variants may remain immunologically active with an activity of over about 1%, over about 10%, over about 25%, over about 50%, over about 60%, over about 70%, over about 80%, over about 90%, over about 95%, or over about 100% of the immunological activity of the native protein.

Conservative modifications to the amino acid sequence of a $\beta_2$-GPI protein generally produce a polypeptide having functional and chemical characteristics similar to those of the original $\beta_2$-GPI proteins. In contrast, substantial modifications in the functional and/or chemical characteristics of a $\beta_2$-GPI protein may be accomplished by selecting substitutions in the amino acid sequence of the $\beta_2$-GPI protein that differ significantly in their effects on maintaining (a) the structure (secondary, tertiary, and/or quaternary) in the area of the substitution or (b) the charge or hydrophobicity of the molecule at the target site. Amino acid sequence modifications can be accomplished by chemical and biological peptide and protein synthetic methods that are well know in the art.

Desired amino acid substitutions (whether conservative or non-conservative) can be determined by those skilled in the art at the time such substitutions are required. For example, amino acid substitutions can be used to identify important residues, to modulate the biological activity of a $\beta_2$-GPI protein, e.g., the binding interactions with $\beta_2$-GPI-specific antibodies, or to decrease unwanted non-specific binding interactions with other molecules in a sample. Suitable amino acid substitutions include, but are not limited to, substituting Ala with Val, Leu, or Ile; substituting Arg with Lys, Gln, or Asn; substituting Asn with Gln; substituting Asp with Glu; substituting Cys with Ser or Ala; substituting Gln with Asn; substituting Glu with Asp; substituting His with Asn, Gln, Lys, or Arg; substituting Ile with Leu, Val, Met, Ala, Phe, or Norleucine; substituting Leu with Norleucine, Ile, Val, Met, Ala, or Phe; substituting Lys with Arg, 1,4-diamino-butyric acid, Gln, or Asn; substituting Met with Leu, Phe, or Ile; substituting Phe with Leu, Val, Ile, Ala, or Tyr; substituting Pro with Ala; substituting Ser with Thr, Ala, or Cys; substituting Thr with Ser; substituting Trp with Tyr or Phe; substituting Tyr with Trp, Phe, Thr, or Ser; and substituting Val with Ile, Met, Leu, Phe, Ala, or Norleucine. The selection of an amino acid for replacement can also be guided by its hydropathic index and/or hydrophilicity.

In addition, the polypeptide may be fused to a homologous polypeptide to form a homodimer or to a heterologous polypeptide to form a heterodimer. Heterologous polypeptides include, but are not limited to: an epitope to allow for the detection and/or isolation of a $\beta_2$-GPI fusion polypeptide, such as, polyhistine at either C- or N-terminal to ease the purification; an enzyme or portion thereof which is catalytically active; a polypeptide which promotes oligomerization, such as a leucine zipper domain; and a polypeptide which increases stability, such as an immunoglobulin constant region.

Fusions can be made either at the amino-terminus or at the carboxyl-terminus of a $\beta_2$-GPI polypeptide. Fusions may be direct with no linker or adapter molecule or may be through a linker or adapter molecule. A linker or adapter molecule may be one or more amino acid residues, typically from about 20 to about 50 amino acid residues. A linker or adapter molecule may also be designed with a cleavage site for a protease to allow for the separation of the fused moieties. It will be appreciated that once constructed, the fusion polypeptides can further be derivatized according to the methods described herein.

The $\beta_2$-GPI protein of the present invention may also be $\beta_2$-GPI derivatives, which is a chemically or biologically modified protein, including protein post-translation modification, such as acylation (i.e., acetylation or formylation), biotinylation, carboxylation, deamination, glutathionylation, glycosylation, lipidation (i.e., farnesylation, gernylgeranylation, prenylation, myristoylation, palmitoylation, or stearoylation), methylation, phosphorylation, sulphation, fucosylation, and ubiquitination. Unless otherwise indicated, the term "$\beta_2$-GPI protein" refers both to native proteins, and variants and derivatives thereof. A protein derivative may be modified in a manner that is different in the type, number, or location of the post-translation modification groups naturally attached to the polypeptide. For example, a derivative may have the number and/or type of glycosylation altered compared to the native protein. The resulting derivative may comprise a greater or a lesser number of N-linked glycosylation sites than the native protein.

The $\beta_2$-GPI polypeptide may also be modified by the covalent attachment of one or more polymers. Typically, the polymer selected is water-soluble so that the protein to which it is attached does not precipitate in an aqueous environment, such as a physiological environment. The polymer may be of any molecular weight and may be branched or unbranched. The polymer each typically has an average molecular weight of between about 1 kDa to about 100 kDa.

Suitable water-soluble polymers or mixtures thereof include, but are not limited to, polyalkylene glycol (such as mono-($C_1$-$C_{10}$)alkoxy-, aryloxy-polyethylene glycol, poly-(N-vinyl pyrrolidone) polyethylene glycol, propylene glycol homopolymers, or polypropylene oxide/ethylene oxide co-polymers), carbohydrate-based polymers (such as dextran or cellulose), polyoxyethylated polyols, and polyvinyl alcohols. Also encompassed by the present invention are bifunctional crosslinking molecules which can be used to prepare covalently attached $\beta_2$-GPI polypeptide multimers.

In general, chemical derivatization may be performed under a suitable condition by reacting a protein with an activated polymer molecule. Methods for preparing chemical derivatives of polypeptides will generally comprise the steps of: (a) reacting the polypeptide with the activated polymer molecule (such as a reactive ester or aldehyde derivative of the polymer molecule) under conditions whereby the $\beta_2$-GPI protein becomes attached to one or more polymer molecules, and (b) obtaining the reaction products. The optimal reaction conditions may vary depending upon the $\beta_2$-GPI protein selected and chemical reagents used, and are generally determined experimentally. The PEGylation of a polypeptide may be carried out using any of the PEGylation reactions known in the art, including, but not limited to, acylation, alkylation, or Michael addition.

Diagnostic Assay

There are many different types of immunoassays suitable for use in the present invention. Any of the well known immunoassays may be adapted to detect the level of $\beta_2$-GPI-specific antibodies in a sample which react with the $\beta_2$-GPI antigens, such as, e.g., enzyme linked immunoabsorbent assay (ELISA), fluorescent immunosorbent assay (FIA), chemical linked immunosorbent assay (CLIA), radioimmuno assay (RIA), immunoblotting, gel diffusion precipitation reactions, immunodiffusion assays, in situ immunoassays (e.g., using colloidal gold, enzyme or radioisotope labels, for example), Western blots, precipitation reactions, agglutination assays (e.g., gel agglutination assays, hemagglutination assays, etc.), complement fixation assays, immunofluorescence assays, protein A assays, and immunoelectrophoresis assays, etc. For a review of the different immunoassays which may be used, see: The Immunoassay Handbook, David Wild, ed., Stockton Press, New York, 1994. A competitive immunoassay with solid phase separation or an immunometric assay for antibody testing is particularly suitable for use in the present invention. See, The Immunoassay Handbook, chapter 2.

In one exemplary embodiment of the invention, the diagnostic assay is an immunometric assay for detecting the level of $\beta_2$-GPI-specific antibodies in a sample. In the immunometric assay, the $\beta_2$-GPI antigens are immobilized on a solid support directly or indirectly through a capture agent, such as anti-$\beta_2$-GPI antibodies. An aliquot of a sample, such as a serum sample, from a subject is added to the solid support and allowed to incubate with the $\beta_2$-GPI antigens on the solid phase. A secondary antibody that recognizes a constant region in the autoantibodies present in the sample which have reacted with the $\beta_2$-GPI antigen is added. When the subject is a human, this secondary antibody is an anti-human immunoglobulin. The secondary antibody which is specific for IgA, IgG, or IgM heavy chain constant regions, or combination thereof, may be employed. After separating the solid support from the liquid phase, the support phase is examined for a detectable signal. The presence of the signal on the solid support indicates that autoantibodies to the native $\beta_2$-GPI proteins present in the sample have bound to the $\beta_2$-GPI antigen on the solid support. Increased optical density or radiolabeled signal when compared to the control samples from normal subjects correlates with a diagnosis of APS in a subject.

Solid supports are known to those skilled in the art and include the walls of wells of a reaction tray (e.g., microtiter plates), test tubes, polystyrene beads, magnetic beads, nitrocellulose strips, membranes, microparticles such as latex particles, glass or silicon chips, sheep (or other animal) red blood cells, duracytes and others. Suitable methods for immobilizing nucleic acids on solid phases include ionic, hydrophobic, covalent interactions and the like. A solid support, as used herein, refers to any material which is insoluble, or can be made insoluble by a subsequent reaction. The solid support can be chosen for its intrinsic ability to attract and immobilize the capture reagent. Alternatively, the solid phase can retain an additional molecule which has the ability to attract and immobilize the capture reagent. The additional molecule can include a charged substance that is oppositely charged with respect to the capture reagent itself or to a charged substance conjugated to the capture reagent. As yet another alternative, the molecule can be any specific binding member which is immobilized upon (attached to) the solid support and which has the ability to immobilize the $\beta_2$-GPI antigen through a specific binding reaction. The molecule enables the indirect binding of the $\beta_2$-GPI antigen to a solid support material before the performance of the assay or during the performance of the assay.

The signal producing system is made up of one or more components, at least one of which is a label, which generate a detectable signal that relates to the amount of bound and/or unbound label, i.e., the amount of label bound or unbound to the $\beta_2$-GPI antigen. The label is a molecule that produces or which may be induced to produce a signal. Examples of labels include fluorescers, enzymes, chemiluminescers, photosensitizers or suspendable particles. The signal is detected and may be measured by detecting enzyme activity, luminescence or light absorbance. Radiolabels may also be used and levels of radioactivity detected and measured using a scintillation counter.

Examples of enzymes which may be used to label the anti-human immunoglobulin include $\beta$-D-galactosidase, horseradish peroxidase, alkaline phosphatase, and glucose-6-phosphate dehydrogenase ("G6PDH"). Examples of fluorescers which may be used to label the anti-human immunoglobulin include fluorescein, isothiocyanate, rhodamines, phycoerythrin, phycocyanin, allophycocyanin, o-phthaldehyde, fluorescamine, and Alexa Fluor® dyes (that is, sulfonated courmarin, rhodamine, xanthene, and cyanine dyes). Chemiluminescers include e.g., isoluminol. For example, the anti-human immunoglobulin may be enzyme labeled with either horseradish peroxidase or alkaline phosphatase.

Enzymes may be covalently linked to $\beta_2$-GPI antigen reactive antibodies for use in the methods of the present invention using well known methods. There are many well known conjugation methods. For example, alkaline phosphatase and horseradish peroxidase may be conjugated to antibodies using glutaraldehyde. Horseradish peroxidase may also be conjugated using the periodate method. Commercial kits for enzyme conjugating antibodies are widely available. Enzyme conjugated anti-human and anti-mouse immunoglobulin specific antibodies are available from multiple commercial sources.

Biotin labeled antibodies may be used as an alternative to enzyme linked antibodies. In such cases, bound antibody would be detected using commercially available streptavidin-horseradish peroxidase detection systems.

Enzyme labeled antibodies produce different signal sources, depending on the substrate. Signal generation involves the addition of substrate to the reaction mixture. Common peroxidase substrates include ABTS (2,2'-azinobis (ethylbenzothiazoline-6-sulfonate)), OPD (O-phenylenediamine) and TMB (3,3',5,5'-tetramethylbenzidine). These substrates require the presence of hydrogen peroxide. p-Nitrophenyl phosphate is a commonly used alkaline phosphatase substrate. During an incubation period, the enzyme gradually converts a proportion of the substrate to its end product. At the end of the incubation period, a stopping reagent is added which stops enzyme activity. Signal strength is determined by measuring optical density, usually via spectrophotometer.

Alkaline phosphatase labeled antibodies may also be measured by fluorometry. Thus in the immunoassays of the present invention, the substrate 4-methylumbelliferyl phosphate (4-UMP) may be used. Alkaline phosphatase dephosphorylated 4-UMP to form 4-methylumbelliferone (4-MU), the fluorophore. Incident light is at 365 nm and emitted light is at 448 nm.

The amount of color, fluorescence, luminescence, or radioactivity present in the reaction (depending on the signal producing system used) is proportionate to the amount of autoantibodies in a sample which react with the $\beta_2$-GPI antigens. Quantification of optical density may be performed using spectrophotometric or fluorometric methods, including flow cytometers. Quantification of radiolabel signal may be performed using scintillation counting.

In another exemplary embodiment, the assay is a competitive immunoassay, which employs one or more $\beta_2$-GPI-specific antibodies that binds to the same epitopes as the $\beta_2$-GPI-specific autoantibodies. In the assay, the $\beta_2$-GPI-specific antibodies and the $\beta_2$-GPI-specific autoantibodies in a sample compete for binding to the $\beta_2$-GPI antigens. Typically, a constant amount of a labeled antibody which is known to bind to $\beta_2$-GPI antigen is incubated with different concentrations of a sample from a subject. The $\beta_2$-GPI-specific antibodies may be monoclonal or polyclonal.

As described herein above, the $\beta_2$-GPI-specific antibodies may be labeled with a fluorescer, enzyme, chemiluminescer, photosensitizer, suspendable particles, or radioisotope. After incubation, bound labeled antibodies are separated from free antibodies. Depending on the signal producing system used and if necessary, an appropriate substrate with which the labeled antibody reacts is added and allowed to incubate. The signal generated by the sample is then measured. A decrease in optical density or radioactivity from before and after addition of the serum sample or between experimental and control samples, is indicative that autoantibodies in the sample have bound to the $\beta_2$-GPI antigen. Decreased optical density or radiolabeled signal when compared to control samples from normal subjects correlates with a diagnosis of APS in a subject.

In an alternative exemplary embodiment of the competitive immunoassay, an indirect method using two antibodies is provided. $\beta_2$-GPI antigen specific antibodies are added first as described in the preceding paragraph with the exception that they are not labeled. They are incubated with different concentrations of a sample from a subject. A constant amount of a second antibody is then added to the mixture of the sample and the first antibody. The second antibody recognizes constant regions of the heavy chains of the first antibody. For example, the second antibody may be an antibody which recognizes constant regions of the heavy chains of mouse immunoglobulin which has reacted with the $\beta_2$-GPI antigens (anti-mouse immunoglobulin). The second antibody may be labeled with a fluorophore, chemilophore or radioisotope, as described above. Free labeled second antibody is separated from bound antibody. If an enzyme-labeled antibody is used, an appropriate substrate with which the enzyme label reacts is added and allowed to incubate. A decrease in optical density or radioactivity from before and after addition of the serum sample in comparison with control samples is indicative that autoantibodies in the serum sample have bound to the $\beta_2$-GPI antigens. Decreased optical density or radioactivity when compared to control samples from normal subject correlates with a diagnosis of a APS in a subject.

In some embodiments, an automated detection assay is utilized. Methods for the automation of immunoassays include those described in U.S. Pat. Nos. 5,885,530, 4,981,785, 6,159,750, and 5,358,691, each of which is herein incorporated by reference. In some embodiments, the analysis and presentation of results is also automated. For example, in some embodiments, software that generates a prognosis based on the presence or absence of a series of proteins corresponding to autoimmune or chronic inflammatory disease markers is utilized.

In some embodiments, the $\beta_2$-GPI specific autoantibody level may be used together with other biological markers as a panel for the diagnosis of heart disease. The panel allows for the simultaneous analysis of multiple markers correlating with AAS. For example, a panel may include markers identified as correlating with AAS in a subject that is likely or not to respond to a given treatment. Depending on the subject, panels may be analyzed alone or in combination in order to provide the best possible diagnosis and prognosis. Markers for inclusion on a panel are selected by screening for their predictive value using any suitable method, including but not limited to, those described in the illustrative examples below.

Data Analysis

In the present invention, a computer-based analysis program may also be used to translate the raw data generated by the detection assay into data of predictive value for a clinician. The clinician can readily access the predictive data using any suitable means. The clinician is then able to immediately utilize the information in order to optimize the care of the subject.

The present invention contemplates any method capable of receiving, processing, and transmitting the information to and from laboratories conducting the assays, information provides, medical personal, and subjects. For example, in some embodiments of the present invention, a sample (e.g., a biopsy or a serum or urine sample) is obtained from a subject and submitted to a profiling service (e.g., clinical lab at a medical facility, genomic profiling business, etc.), located in any part of the world (e.g., in a country different than the country where the subject resides or where the information is ultimately used) to generate raw data. Where the sample comprises a tissue or other biological sample, the subject may visit a medical center to have the sample obtained and sent to the profiling center, or subjects may collect the sample themselves (e.g., a urine sample) and directly send it to a profiling center. Where the sample comprises previously determined biological information, the information may be directly sent to the profiling service by the subject (e.g., an information card containing the information may be scanned by a computer and the data transmitted to a computer of the profiling center using an electronic communication system). Once received by the profiling service, the sample is processed and a profile is produced, specific for the diagnostic or prognostic information desired for the subject.

The profile data is then prepared in a format suitable for interpretation by a treating clinician. For example, rather than providing raw expression data, the prepared format may represent a diagnosis or risk assessment (e.g., likelihood of a liver disease such as HCC to respond to a specific therapy) for the subject, along with recommendations for particular treatment options. The data may be displayed to the clinician by any suitable method. For example, in some embodiments, the profiling service generates a report that can be printed for the clinician (e.g., at the point of care) or displayed to the clinician on a computer monitor.

In some embodiments, the information is first analyzed at the point of care or at a regional facility. The raw data is then sent to a central processing facility for further analysis and/or to convert the raw data to information useful for a clinician or patient. The central processing facility provides the advantage of privacy (all data is stored in a central facility with uniform security protocols), speed, and uniformity of data analysis. The central processing facility can then control the fate of the data following treatment of the subject. For example, using an electronic communication system, the central facility can provide data to the clinician, the subject, or researchers.

In some embodiments, the subject is able to directly access the data using the electronic communication system. The subject may chose further intervention or counseling based on the results. In some embodiments, the data is used for research use. For example, the data may be used to further optimize the inclusion or elimination of markers as useful indicators of a particular condition or severity of disease.

EXAMPLES

Autoantibodies targeting $\beta_2$-Glycoprotein I ($\beta_2$-GPI), a component of the atherosclerotic plaque, are commonly found in patients with acute ischemic syndromes. Serum samples from APS (Antiphospholipid Syndrome) patients and from cardiovascular patients exhibiting acute atherosclerotic syndromes were analyzed for IgG and IgA antibodies in both anti-$\beta_2$-GPI and anti-cardiolipin (aCL) ELISA assays. All of the APS samples used were positive in both assays. Serum samples from 382 cardiovascular patients were also analyzed for IgG and IgA antibodies in the same assays. In sharp contrast to the APS samples, it was found that only 1% of the samples from cardiovascular patients were positive for IgA aCL, and 1.6% positive for IgG aCL, whereas 35.6% were positive for IgA anti-$\beta_2$-GPI and only 1.6% for IgG anti-$\beta_2$-GPI. The antigenic specificity of 29 serum samples from cardiovascular patients was evaluated. Six different recombinant domain-deleted mutants (DM) of human $\beta_2$-GPI and full-length human $\beta_2$-GPI (wild-type), were used in competitive inhibition assays to inhibit the autoantibodies from binding in the anti-$\beta_2$-GPI ELISA assays. Domain-deleted mutants D--345 and D---45 inhibited the binding in the IgA anti-$\beta_2$-GPI assay suggesting that these autoantibodies recognize domain 4 of the $\beta_2$-GPI molecule. These results demonstrated that IgA anti-$\beta_2$-GPI autoantibodies from atherosclerotic patients are distinct from IgA autoantibodies found in APS samples.

Example 1

This example demonstrates that the predominant antibody profile exhibited by APS patients (cardiolipin IgG positive/ $\beta_2$-GPI IgG/IgA positive) differed from the predominant profile exhibited by atherosclerotic patients with acute ischemic disease (cardiolipin IgG/IgA negative/$\beta_2$-GPI IgA positive) because of differing domain specificity of the APS and atherosclerosis patient's antibodies. Using a series of full-length $\beta_2$-GPI and $\beta_2$-GPI Dms, a large number of serum samples from patients with APS and various atherosclerotic populations were tested for IgG, IgA, and IgM antibodies to these constructs by using a competitive inhibition ELISA. All specimens were also tested for IgG, IgA, and IgM aCL antibodies. This experiment demonstrated that 29 of 29 IgA anti-$\beta_2$-GPI positive samples from atherosclerosis patients specifically recognized domain 4 of $\beta_2$-GPI.

Materials and Methods

Recombinant $\beta_2$-GPI

The recombinant $\beta_2$-GPI and $\beta_2$-GPI domain-deleted mutants (Dms) used are as previously described (Igarashi M, et al., *Blood* 87(8):3262-3270 (1996). Briefly, TN5 insect cells were infected with high titer viral stock produced in Sf9 insect cells. Each construct contained a 6his tail that was used for purifying the protein from culture media. The nomenclature for domain deletion mutants uses numbers to indicate the presence of domains while a dash symbolizes the domain is missing. Thus D--345 is the name given to the recombinant protein that contains domains 3, 4 and 5 while lacking domains 1 and 2.

Patient Sample Selection

The diagnosis of each syndrome described was done according to clinical presentation, ultrasound, angiography or magnetic angioresonance studies. Patients were enrolled consecutively in a tertiary center (University Hospital). Patients with infective endocarditis, osteonecrosis, neoplasms, cerebral hemorrhage, infection by HIV or *treponema pallidum*, presence of known heritable causes of thrombosis such as homocistinuria or factor V (Leiden) mutation, previous diagnosis of APS, or other connective tissue disorder (CTD) were excluded. Control patients were recruited from patients admitted to the Orthopedic clinic for fractures or musculoligamentous disorders and without acute myocardial infarction, stroke, or other cardiac conditions (Ranzolin A, et al., *Arg Bras Cardiol*, 83(2): 141-4; 137-140 (2004); Staub H L et al., *Arg Bras Neuropsiquiat* 61(3B): 757-63 (2003)).

A total of 511 archived specimens consisting of 382 sera from individuals with various atherosclerosis conditions and 129 sera from individuals with anti-phospholipid syndrome were studied. The atherosclerosis group included sera from individuals with peripheral arterial disease (117), acute coronary syndrome (117), and acute myocardial infarction (90). Ten samples were randomly selected from APS patients that were positive for both IgG and IgA in the anti-$\beta_2$-GPI ELISA, and 29 samples from atherosclerosis patients that were positive for IgA in the anti-$\beta_2$-GPI ELISA.

Anti-$\beta_2$-GPI and Anti-Cardiolipin ELISA

All samples, both from the APS and cardiovascular patients, were tested for the presence of anticardiolipin (aCL) antibodies and anti-$\beta_2$-GPI antibodies by ELISA. Specimens were first tested for the presence of IgG, IgA, or IgM aCL and $\beta_2$-GPI antibodies using polyvalent aCL and anti-$\beta_2$-GPI screening ELISA tests. All ELISA kits used in this study were manufactured by INOVA Diagnostics (INOVA Diagnostics, San Diego, Calif.) and run according to the manufacturer's instructions.

Competitive Inhibition ELISA

Tests were performed using the appropriate (IgG and/or IgA) anti-$\beta_2$-GPI ELISA kit from INOVA Diagnostics. Each serum was titered to determine the dilution required to give approximately 80% of maximum binding. Test inhibitors were diluted in the sample dilution buffer provided in the kits and 25 µl of each dilution or sample diluent alone was added to the wells. The serum samples were diluted in sample dilution buffer and 25 µl of a constant dilution was added to the wells. The contents of the wells were mixed and plates were incubated at room temperature for 30 minutes. Wells were washed 3 times with the wash buffer provided in the kits, 50 µl of the HRP conjugated anti-IgG or IgA added, incubated for 30 minutes, washed 3 times with wash buffer and 50 µl of substrate solution was added. Wells were incubated at room temperature for 30 minutes and 50 µl of stop solution was added. The OD 450 for each well was determined in an Anthos Labtec HT2 microplate reader (Salzburg, Austria). The percent inhibition was determined as follows: [(mean $A_{450}$ obtained from the control wells without inhibitor less $A_{450}$ of background)–($A_{450}$ obtained in the presence of inhibitor less $A_{450}$ of background)/mean $A_{450}$ obtained from the control wells without inhibitor less $A_{450}$ of background]× 100.

Results

Anti-$\beta_2$-GPI and Anti-Cardiolipin

Serum samples from APS and cardiovascular patients were analyzed for IgG and IgA autoantibodies in both the anti-$\beta_2$-GPI and the anti-cardiolipin (aCL) assays. Almost 80% of the APS samples were positive by polyvalent IgG/IgA/IgM aCL and $\beta_2$-GPI screening assays (Table 1).

TABLE 1

Frequency of aCL and anti-$\beta_2$-GPI antibodies in APS and Cardiovascular Groups by ELISA testing

| Total sera = 511 | APS patients (n = 129) | Cardiovascular patients (n = 382) |
|---|---|---|
| aCL Screen (IgG/IgA/IgM) | 78% | 12% |
| anti-$\beta_2$-GPI Screen (IgG/IgA/IgM) | 79% | 46% |
| aCL IgG | 64% | 1% |
| aCL IgA | 9% | 1% |
| Anti-$\beta_2$-GPI IgG | 43% | 1% |
| Anti-$\beta_2$-GPI IgA | 48% | 33% |

Specific isotype testing of the APS sera revealed that approximately 64% were IgG and 9% were IgA ACA antibody positive, while 43% were IgG and 48% were IgA anti-$\beta_2$-GPI positive. Serum samples from 370 cardiovascular patients were similarly tested for total (IgG/IgA/IgM) and specific IgG and IgA antibodies in both the aCL and anti-$\beta_2$-GPI assays. In sharp contrast to the APS samples, where IgG aCL and IgG anti-$\beta_2$-GPI antibodies were found in 64% and 43% of the specimens, respectively, it was found that IgG aCL and IgG anti-$\beta_2$-GPI antibodies were present in only 1% of the samples from cardiovascular patients. Even more striking was the observation that while the pattern of reactivity for IgA aCL and IgA anti-$\beta_2$-GPI was similar in the APS and cardiovascular patients (both had low levels of IgA aCL and moderate levels of IgA anti-$\beta_2$-GPI), IgA anti-$\beta_2$-GPI was the only major antibody present in the cardiovascular group. In contrast, the APL patients had moderate levels of antibodies to IgG aCL, IgG anti-$\beta_2$-GPI, and IgA anti-$\beta_2$-GPI (Table 1).

Epitope(s) of $\beta_2$-GPI Recognized by Both IgG and IgA Anti-$\beta_2$-GPI I from APS Patients.

Recombinant $\beta_2$-GPI and two deletion mutants were used to determine the antigenic specificity of both the IgG and IgA autoantibodies from 10 different APS patients. Each recombinant form of $\beta_2$-GPI was tested, in a dose-dependent fashion, for its ability to inhibit these autoantibodies from binding to full length $\beta_2$-GPI (Table 2, FIG. 1).

TABLE 2

Competitive inhibition assay using 10 different APS serum samples with indicated recombinant B2GPI and deletion mutants.

| | IgG | | | | | |
|---|---|---|---|---|---|---|
| Antibody | D12345[1] | | D12--- | | D---45 | |
| Number | Max[2] | 50%[3] | Max | 50% | Max | 50% |
| 6612 | 89 | 9.5 | 98 | 24.0 | 17.0 | >125 |
| 6626 | 88 | 31.8 | 90 | 88.0 | 3.5 | >125 |
| 6635 | 95 | 11.8 | 96 | 29.5 | 3.0 | >125 |
| 6647 | 92 | 25.8 | 94 | 66.0 | 5.0 | >125 |
| 6656 | 64 | 38.4 | 67 | 85.0 | 10.0 | >125 |
| 6666 | 79 | 27.2 | 85 | 20.3 | 2.4 | >125 |
| 6674 | 90 | 20.5 | 94 | 52.0 | 12.0 | >125 |
| 7002 | 58 | 53.7 | 53 | 178.0 | 7.0 | >125 |
| 7005 | 77 | 23.5 | 71 | 58.0 | 1.9 | >125 |
| 7010 | 83 | 15.8 | 86 | 41.6 | 14.0 | >125 |

TABLE 2-continued

Competitive inhibition assay using 10 different APS serum samples with indicated recombinant B2GPI and deletion mutants.

| | IgA | | | | | |
|---|---|---|---|---|---|---|
| Antibody | D12345 | | D12--- | | D---45 | |
| Number | Max | 50% | Max | 50% | Max | 50% |
| 6612 | 80 | 13.1 | 74 | 36 | 28 | >125 |
| 6626 | 62 | 42.4 | 39 | >125 | 61 | >125 |
| 6635 | 57 | 44.7 | 67 | 29.6 | 0 | >125 |
| 6647 | 68 | 30.7 | 58 | 66.4 | 0.7 | >125 |
| 6656 | 74 | 24.3 | 42 | >125 | 40 | >125 |
| 6666 | 48 | 67.3 | 42 | >125 | 11 | >125 |
| 6674 | 85 | 39.9 | 88 | 39.9 | 4 | >125 |
| 7002 | 29 | 116.3 | 21 | >125 | 0 | >125 |
| 7005 | 35 | 50.6 | 45 | >125 | 40 | >125 |
| 7010 | 63 | 16.7 | 59 | 50 | 12 | >125 |

>= Highest concentration tested.
[1]= Domains included in construct.
[2]= Maximum Inhibition observed at concentrations tested.
[3]= Concentration (micromolar) to give 50% inhibition.

Only those constructs that contained domain 1 inhibited both the IgG and IgA autoantibodies. As shown in Table 2, both the IgG and IgA anti-$\beta_2$-GPI binding antibodies from all 10 patients were inhibited by both constructs that contain domain 1. None of the samples were effectively inhibited, even at the highest concentration tested, by the construct that lacked domain 1. $ID_{50}$ values for mutants that contain domain 1 ranged from 1 to 50 μM for the IgG antibody and 13 to 100 μM for the IgA antibody. By contrast the mutant that did not contain domain 1 (D---45) did not effectively inhibit either the IgG nor the IgA antibody.

Epitope(s) of $\beta_2$-GPI Recognized by IgA Anti-$\beta_2$-GPI from Patients with Acute Cardiovascular Syndromes.

The differing $\beta_2$-GPI and aCL profile of the APS and cardiovascular sera (Table 1) suggested to us that the IgA anti-$\beta_2$-GPI antibodies in cardiovascular patients may be distinct from those present in APS patients and might target a different domain on the $\beta_2$-GPI protein.

Twenty nine samples from the cardiovascular patient cohort were selected which were IgA anti-$\beta_2$-GPI antibody positive and aCL IgG, aCL IgM, and with the exception of one sera, aCL IgA negative. The detailed $\beta_2$-GPI and aCL profiles of these sera are shown in Table 3.

TABLE 3

Anti-aCL and anti-$\beta_2$-GPI profile of samples from cardiovascular patients[1] for inhibition study.

| Sample | $\beta_2$-GPI IgA Units | $\beta_2$-GPI IgG Units[2] | $\beta_2$-GPI IgM Units | aCl IgA Units | aCl IgG Units | ACl IgM Units |
|---|---|---|---|---|---|---|
| ACS-52 | 58.9 | 0 | 10.1 | n.t. | n.t. | n.t. |
| ACS-53 | 20.7 | 0 | 4.0 | n.t. | n.t. | n.t. |
| ACS-54 | 33.1 | 9.6 | 0 | n.t. | n.t. | n.t. |
| ACS-58 | 86.4 | 0 | 5.3 | n.t. | n.t. | n.t. |
| ACS-65 | 234.4 | 0 | 4.0 | n.t. | n.t. | n.t. |
| ACS-67 | 38.7 | 0 | 0 | n.t. | n.t. | n.t. |
| ACS-71 | 77.6 | 0 | 0 | n.t. | n.t. | n.t. |
| ACS-74 | 154.8 | 0 | 5.7 | n.t. | n.t. | n.t. |
| ACS-104 | 23.7 | 0 | 58.5 | n.t. | n.t. | n.t. |
| ACS-136 | 32.0 | 64.4 | 0.2 | n.t. | n.t. | n.t. |
| ACS-144 | 28.3 | 3.3 | 16.9 | n.t. | n.t. | n.t. |
| CAS-5 | 65.4 | 0 | 2.8 | n.t. | n.t. | n.t. |
| CAS-6 | 55.5 | 1.2 | 0 | n.t. | n.t. | n.t. |
| CAS-8 | 61.2 | 0 | 0 | n.t. | n.t. | n.t. |

TABLE 3-continued

Anti-aCL and anti-β$_2$-GPI profile of samples from cardiovascular patients[1] for inhibition study.

| Sample | β$_2$-GPI IgA Units | β$_2$-GPI IgG Units[2] | β$_2$-GPI IgM Units | aCl IgA Units | aCl IgG Units | ACl IgM Units |
|---|---|---|---|---|---|---|
| CAS-13 | 39.9 | 1.7 | 11.7 | n.t. | n.t. | n.t. |
| CAS-15 | 130.1 | 0.1 | 0 | n.t. | n.t. | n.t. |
| CAS-18 | 35.5 | 0 | 0 | n.t. | n.t. | n.t. |
| CAS-28 | 60.5 | 0 | 0 | n.t. | n.t. | n.t. |
| CAS-29 | 51.8 | 4.1 | 5.7 | n.t. | n.t. | n.t. |
| MI-5 | 70.0 | 0 | 25.6 | n.t. | n.t. | n.t. |
| MI-7 | 90.4 | 0 | 0 | n.t. | n.t. | n.t. |
| MI-10 | 183.9 | 0 | 25.4 | n.t. | n.t. | n.t. |
| MI-15 | 58.4 | 0 | 77.4 | n.t. | n.t. | n.t. |
| MI-37 | 32.7 | 0 | 41.2 | n.t. | n.t. | n.t. |
| MI-45 | 25.5 | 0 | 11.6 | n.t. | n.t. | n.t. |
| PAD-30 | 27.6 | 0 | 0 | n.t. | n.t. | n.t. |
| PAD-39 | 22.1 | 0 | 0 | n.t. | n.t. | n.t. |
| PAD-42 | 45.5 | 0 | 0 | 27.9 | n.t. | n.t. |
| PAD-101 | 26.4 | 3.0 | 25.4 | n.t. | n.t. | n.t. | n.t. = Specimens testing negative on aCL screening assay were not tested on isotype-specific assays.
[1] = ACS: Acute Coronary Syndrome. MI: Myocardial Infarction. CAS: Carotid Artery Study. PAD: Peripheral Artery Disease.
[2] = β$_2$-GPI results with negative values (resulting from extrapolation at bottom of the standard curve) were assigned a value of 0.

Seven different recombinant β$_2$-GPI mutant proteins were used to determine the antigenic specificity of the IgA β$_2$-GPI binding antibodies from 29 different samples from patients with various cardiovascular conditions, including acute cardiac syndrome (11), acute myocardial infarction (6), carotid artery disease (8), and peripheral artery disease (4). Each mutant recombinant β$_2$-GPI protein was tested, in a dose-dependent fashion, for its ability to inhibit the IgA antibody from binding to full-length β$_2$-GPI (Table 4).

TABLE 4

Competitive inhibition assays using 29 different serum samples, from patients with cardiovascular problems[1], with indicated recombinant B2GP1 and deletion-mutants.

| | 12345[2] | | 12--- | | 123-- | | 1234- | | ---345 | | ---45 | | ----5 | |
|---|---|---|---|---|---|---|---|---|---|---|---|---|---|---|
| Ab# | Max[3] | 50%[4] | Max | 50% | Max | 50% | Max | 50% | Max | 50% | Max | 50% | Max | 50% |
| ACS-104 | 62 | 20 | 0 | >125 | 13 | >83 | 0 | >63 | 79 | 30 | 76 | 24 | 10 | >250 |
| ACS-136 | 74 | 12 | 3 | >125 | 0 | >83 | 0 | >63 | 72 | 6 | 76 | 26 | 3 | >250 |
| ACS-144 | 52 | 12 | 12 | >125 | 12 | >83 | 8 | >63 | 63 | 6 | 68 | 7 | 9 | >250 |
| ACS-52 | 70 | 17 | 0 | >125 | 14 | >83 | 30 | >63 | 86 | 6 | 87 | 2 | 21 | >250 |
| ACS-53 | 56 | 23 | 15 | >125 | 12 | >83 | 24 | >83 | 76 | 10 | 80 | 14 | 10 | >250 |
| ACS-54 | 71 | 5 | 11 | >125 | 0 | >83 | 0 | >63 | 67 | 3 | 85 | 2 | 3 | >250 |
| ACS-58 | 57 | 24 | 0 | >125 | 7 | >83 | 24 | >63 | 84 | 20 | 90 | 16 | 2 | >250 |
| ACS-65 | 82 | 12 | 0 | >125 | 18 | >83 | 88 | 5 | 92 | 4 | 94 | 8 | 0 | >250 |
| ACS-67 | 65 | 21 | 8 | >125 | 2 | >83 | 49 | >63 | 75 | 21 | 83 | 23 | 20 | >250 |
| ACS-71 | 72 | 12 | 18 | >125 | 7 | >83 | 13 | >63 | 90 | 4 | 93 | 4 | 49 | 227 |
| ACS-74 | 69 | 10 | 3 | >125 | 2 | >83 | 15 | >63 | 90 | 5 | 91 | 1 | 29 | >250 |
| CAS-13 | 54 | 34 | 7 | >125 | 0 | >83 | 10 | >63 | 74 | 17 | 72 | 33 | 15 | >250 |
| CAS-15 | 83 | 2 | 0 | >125 | 1 | >83 | 0 | >63 | 92 | 2 | 91 | 17 | 11 | >250 |
| CAS-18 | 72 | 24 | 0 | >125 | 13 | >83 | 0 | >63 | 85 | 31 | 82 | 46 | 0 | >250 |
| CAS-28 | 65 | 18 | 7 | >125 | 22 | >83 | 39 | >63 | 84 | 26 | 84 | 29 | 0 | >250 |
| CAS-29 | 63 | 26 | 8 | >125 | 17 | >83 | 33 | >63 | 76 | 36 | 75 | 28 | 0 | >250 |
| CAS-5 | 70 | 29 | 0 | >125 | 19 | >83 | 29 | >63 | 90 | 6 | 84 | 20 | 0 | >250 |
| CAS-6 | 68 | 24 | 14 | >125 | 14 | >83 | 27 | >63 | 78 | 6 | 77 | 17 | 15 | >250 |
| CAS-8 | 75 | 23 | 14 | >125 | 0 | >83 | 6 | >63 | 88 | 6 | 87 | 17 | 0 | >250 |
| MI-10 | 74 | 14 | 8 | >125 | 12 | >83 | 64 | 43 | 90 | 13 | 89 | 4 | 0 | >250 |
| MI-15 | 71 | 16 | 6 | >125 | 19 | >83 | 25 | >63 | 71 | 34 | 80 | 12 | 19 | >250 |
| MI-37 | 37 | 52 | 0 | >125 | 0 | >83 | 0 | >63 | 50 | 7 | 58 | 16 | 2 | >250 |
| MI-45 | 60 | 27 | 5 | >125 | 16 | >83 | 20 | >63 | 67 | 38 | 66 | 8 | 0 | >250 |
| MI-5 | 73 | 18 | 30 | >125 | 0 | >83 | 0 | >63 | 90 | 2 | 58 | 5 | 0 | >250 |
| MI-7 | 85 | 2 | 0 | >125 | 35 | >83 | 48 | 55 | 76 | 21 | 90 | 8 | 56 | 80 |
| PAD-101 | 27 | >50 | 3 | >125 | 0 | >83 | 14 | >63 | 67 | 51 | 72 | 55 | 6 | >250 |
| PAD-30 | 57 | 24 | 0 | >125 | 19 | >83 | 58 | 41 | 78 | 30 | 79 | 24 | 0 | >250 |
| PAD-39 | 59 | 19 | 14 | >125 | 10 | >83 | 54 | 46 | 75 | 30 | 77 | 24 | 0 | >250 |
| PAD-42 | 40 | >50 | 9 | >125 | 6 | >83 | 9 | >63 | 79 | 24 | 83 | 29 | 14 | >250 |

> = Greater than highest concentration tested
[1] = ACS: Acute Coronary Syndrome. MI: Myocardial Infarction. CAS: Carotid Artery Study. PAD: Peripheral Artery Disease.
[2] = Domains included in construct.
[3] = Maximum Inhibition observed at concentrations tested.
[4] = Concentration (μM) to give 50% inhibition.

Figure 2:
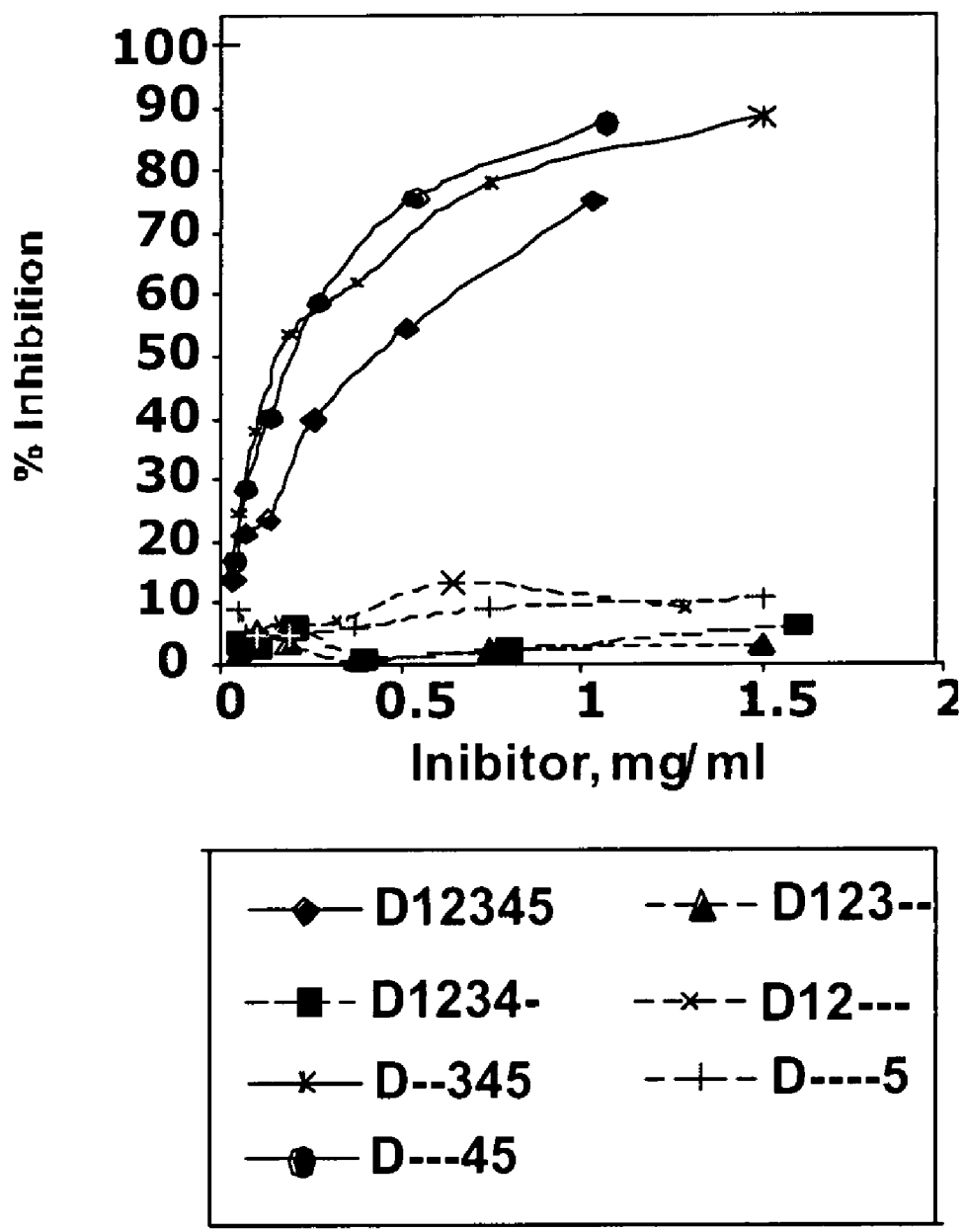
FIG. 2 depicts: Competitive inhibition of IgA anti-$\beta_2$-GPI of ACS-71 from binding to $\beta_2$-GPI by recombinant $\beta_2$-GPI and deletion mutants. A constant amount of antibody was mixed with varying concentrations of inhibitors in wells coated with $\beta_2$-GPI. Recombinant $\beta_2$-GPI and deletion mutants were used as inhibitors.

An example of the results is shown graphically in FIG. 2. With the exception of the full-length construct, only the D--345 and D---45 constructs inhibited these IgA antibodies. Four of the 29 samples were also inhibited, albeit to a much lesser extent, by the D1234-construct. Only one of the samples was also inhibited by the D----5 construct. $ID_{50}$ values for the D--345 and D---45 mutants ranged from 1 to 55 μM. By contrast, the D12--- and D123---mutants did not effectively inhibit the binding of any of the 29 samples tested.

Discussion

It has been previously shown that the antigenic specificity of the IgG autoantibodies found in APS patients recognize domain 1 of the $β_2$-GPI molecule (Iverson, G M et al., *PNAS* 95: 15542-15546 (1998); Iverson, G M, et al., *J. Immunol.* 169:7097-7103 (2002)). The antigenic specificity of the IgA autoantibodies from APS patients however, was not known. The inhibition studies reported here (FIG. 1, Table 2) clearly show that the antigenic specificity of the battery of 10 APS samples studied in this report are directed toward an epitope that is contained within domain 1 of the $\beta_2$-GPI molecule. Thus, the antigenic specificity of both the IgG and IgA autoantibodies found in APS patients is domain 1.

This experiment also shows (FIG. 2 and Table 3) that IgA $\beta_2$-GPI binding antibodies from patients with several types of AAS (acute myocardial infarction, acute coronary syndrome, "carotid artery study", and peripheral artery disease) recognize an epitope on domain 4 of the $\beta_2$-GPI molecule. This should not be confused with earlier studies that purported to show autoantibodies from APS patients recognize domain 4 of $\beta_2$-GPI (Igarashi M., et al, Blood, 87 (8): 3262-70 (1996); George J, et al., J Immunol. 160(8):3917-3923 (1998)). These studies were designed to study the antigenic specificity of IgG, not IgA, autoantibodies.

The Dms that contained domain 4 inhibited in a similar, but not identical pattern, among the various samples tested. For example, only 4 were inhibited by the D1234-construct. This suggests that these antibodies recognize comparable, but distinguishable, epitopes present on domain 4. A recent molecular simulation derived from $\beta_2$-GPI crystal structure supports this possibility. This study suggested 2 discontinuous antigenic sequences in Domain 4$\beta_2$-GPI (Kasahara H, et al., *Int. Immunol.* 17:1533-1542 (2005)). Domain 4 may have different conformational states when present in constructs containing different domains. For example, a few samples recognized domain 4 when domain 5 was absent, while the majority only recognized domain 4 when domain 5 was present. Thus, these antibodies may recognize an epitope on domain 4 that is affected by the presence of additional domains. This interpretation was also supported by the simulation experiments.

Previously it has been shown that the orientation of $\beta_2$-GPI on the ELISA plate is important for the binding of anti-$\beta_2$-GPI autoantibodies when measured by ELISA. (George J, et al., *J. Immunol.* 160(8):3917-3923 (1998)) This could explain why these samples recognize $\beta_2$-GPI when adsorbed onto plastic plates, but do not bind $\beta_2$-GPI when adsorbed onto cardiolipin. The binding of $\beta_2$-GPI to cardiolipin via domain 5 may give a different orientation than when bound to plastic. Binding via domain 5 may alter either the availability of domain 4 or the configuration of domain 4, or both. However, the orientation of the $\beta_2$-GPI molecule when adsorbed onto plastic is not completely understood. It is conceivable that sufficient numbers of molecules adsorb to the plastic in such an orientation that domain 4 is neither hindered, that is available for antibody, nor has its conformation altered enough to negate the binding of these antibodies.

Example 2

A clinical study was performed using an ELISA assay to detect domain 4-specific antibodies using a domain 4/5 combined antigen using 218 clinically characterized sera. The cohort included healthy control individuals (n=30), patients with cardiac stents (without symptoms, n=28; symptomatic, n=23), and patients with acute stroke (ischemic stroke and transient Ischemic attack; without intracerebral hemorrhage, n=137). The mean IgA antibody value for the healthy control population was 14.1 units, compared to 26.5 units for the patients with stents and 29.5 for patients having an acute stroke (Table 5).

TABLE 5

ELISA assays using 218 different serum samples

| | Number of sera tested | | |
|---|---|---|---|
| | 30 | 51 | 137 |
| Patient diagnosis | Control | Stent | Acute stroke |
| Mean value of IgA Domain 4 and 5 of $\beta_2$-GPI antibodies | 14.09 | 26.46 | 29.54 |

The examples set forth above are provided to give those of ordinary skill in the art with a complete disclosure and description of how to make and use the preferred embodiments of the compositions, and are not intended to limit the scope of what the inventors regard as their invention. Modifications of the above-described modes (for carrying out the invention that are obvious to persons of skill in the art) are intended to be within the scope of the following claims. All publications, patents, and patent applications cited in this specification are incorporated herein by reference.

What is claimed is:

1. A method of detecting an autoantibody in a subject suspected of having an acute atherosclerotic syndrome comprising the steps of:
   a) obtaining a serum or plasma sample from the subject, wherein the serum or plasma sample may contain IgA autoantibodies specific for $\beta_2$-Glycoprotein I ($\beta_2$-GPI);
   b) contacting the serum or plasma sample with a polypeptide consisting of $\beta_2$-GPI domain 4 and domain 5 to form a complex between the polypeptide and the IgA autoantibodies;
   c) detecting the IgA antibodies autoantibodies in the complex to establish a level of IgA autoantibodies in the serum or plasma; and
   d) comparing the level of IgA autoantibodies in the complex to a control level of IgA autoantibodies in serum or plasma from healthy control individuals;
   wherein if the level of IgA autoantibodies in the complex is greater than the control level, this indicates that the subject may have an acute atherosclerotic syndrome.

* * * * *

UNITED STATES PATENT AND TRADEMARK OFFICE
CERTIFICATE OF CORRECTION

PATENT NO.      : 7,745,146 B2
APPLICATION NO. : 11/881426
DATED           : June 29, 2010
INVENTOR(S)     : G. Michael Iverson et al.

It is certified that error appears in the above-identified patent and that said Letters Patent is hereby corrected as shown below:

Column 26, line 15 c) reads "detecting the IgA antibodies autoantibodies in the complex"
should read
--detecting the IgA autoantibodies in the complex--

Signed and Sealed this
Ninth Day of April, 2013

Teresa Stanek Rea
*Acting Director of the United States Patent and Trademark Office*